United States Patent
Lee et al.

(10) Patent No.: US 9,936,929 B2
(45) Date of Patent: Apr. 10, 2018

(54) X-RAY IMAGING APPARATUS AND CONTROL METHOD THEREOF

(71) Applicants: SAMSUNG ELECTRONICS CO., LTD., Suwon-si (KR); SAMSUNG LIFE PUBLIC WELFARE FOUNDATION, Seoul (KR)

(72) Inventors: Jae Hak Lee, Yongin-si (KR); Myung Jin Chung, Seoul (KR); Young Hun Sung, Hwaseong-si (KR)

(73) Assignees: SAMSUNG ELECTRONICS CO., LTD., Suwon-si (KR); SAMSUNG LIFE PUBLIC WELFARE FOUNDATION, Seoul (KR)

( * ) Notice: Subject to any disclaimer, the term of this patent is extended or adjusted under 35 U.S.C. 154(b) by 370 days.

(21) Appl. No.: 14/302,855

(22) Filed: Jun. 12, 2014

(65) Prior Publication Data
US 2014/0369464 A1    Dec. 18, 2014

(30) Foreign Application Priority Data

Jun. 12, 2013    (KR) .......................... 10-2013-0067424

(51) Int. Cl.
*A61B 6/02*    (2006.01)
*A61B 6/00*    (2006.01)

(52) U.S. Cl.
CPC .............. *A61B 6/503* (2013.01); *A61B 6/025* (2013.01); *A61B 6/5288* (2013.01); *A61B 6/022* (2013.01); *A61B 6/4035* (2013.01); *A61B 6/4441* (2013.01); *A61B 6/466* (2013.01); *A61B 6/482* (2013.01)

(58) Field of Classification Search
CPC ....... A61B 6/503; A61B 6/025; A61B 6/5288; A61B 6/022; A61B 6/4035; A61B 6/4441; A61B 6/466; A61B 6/482
See application file for complete search history.

(56) References Cited

U.S. PATENT DOCUMENTS

| | | | |
|---|---|---|---|
| 5,903,664 A | 5/1999 | Hartley et al. | |
| 6,628,743 B1* | 9/2003 | Drummond | A61B 6/032 378/15 |
| 8,740,798 B2* | 6/2014 | Hamada | A61B 8/06 382/128 |
| 2004/0136490 A1* | 7/2004 | Edic | A61B 6/032 378/4 |
| 2005/0251013 A1 | 11/2005 | Krishnan et al. | |
| 2006/0293579 A1* | 12/2006 | Schmitt | A61B 6/481 600/407 |

(Continued)

FOREIGN PATENT DOCUMENTS

KR    10-1060348 B1    8/2011

*Primary Examiner* — Courtney Thomas
(74) *Attorney, Agent, or Firm* — Sughrue Mion, PLLC

(57) ABSTRACT

Disclosed herein are an X-ray imaging apparatus and a control method thereof in which a clear 3D volume of an object may be acquired when the 3D volume of the object is reconstructed from X-ray images acquired by radiating X-rays to the object. The X-ray imaging apparatus includes an image processing unit configured to acquire a plurality of X-ray images of an object from converted electrical signals, group the plurality of X-ray images into groups of X-ray images acquired from the same cardiac phase, and perform image reconstruction of each of the groups acquired as a result of the grouping.

20 Claims, 12 Drawing Sheets

(56) References Cited

U.S. PATENT DOCUMENTS

| | | | |
|---|---|---|---|
| 2008/0221442 A1* | 9/2008 | Tolkowsky | A61B 6/5217 600/425 |
| 2009/0097731 A1 | 4/2009 | Sanada et al. | |
| 2010/0174191 A1 | 7/2010 | Lin et al. | |
| 2013/0230136 A1* | 9/2013 | Sakaguchi | H04N 13/00 378/41 |

* cited by examiner

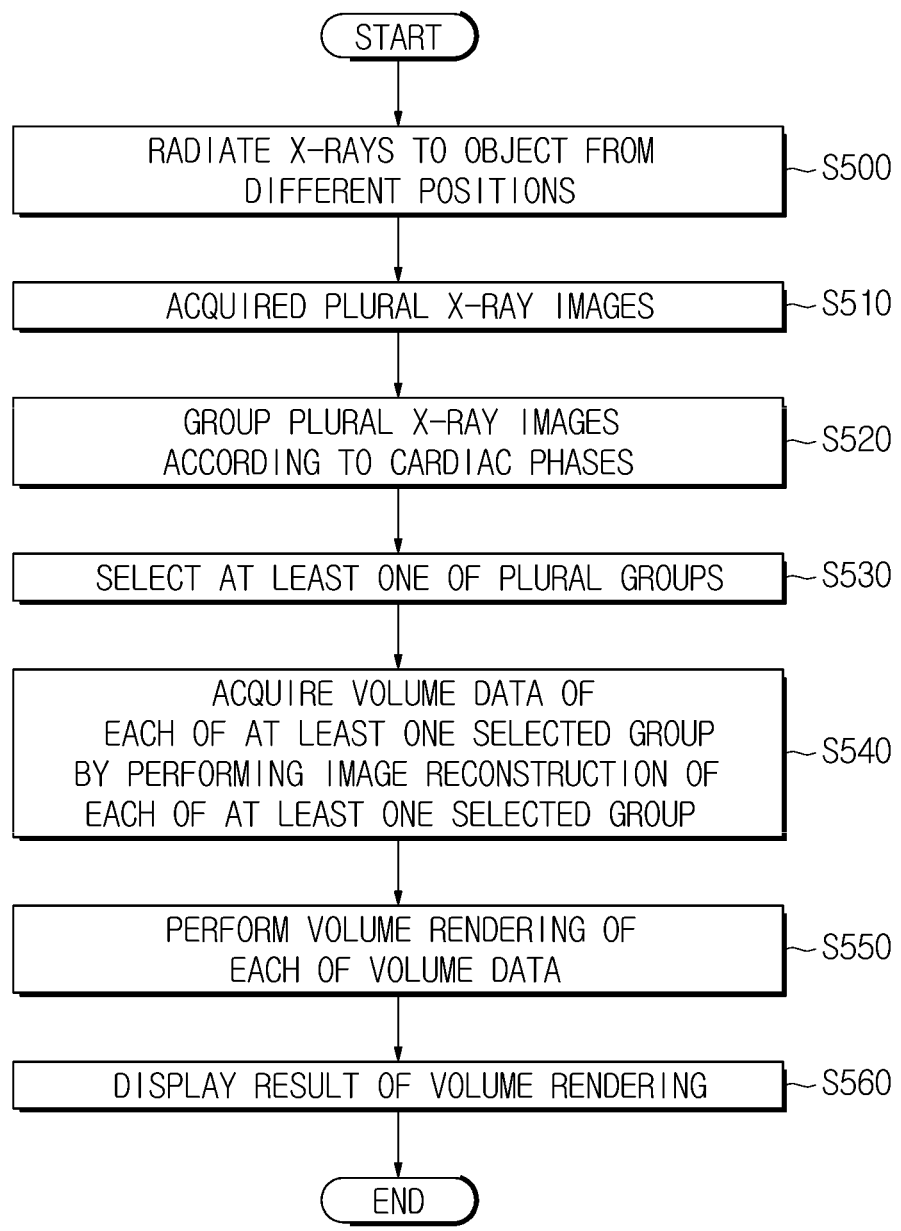

X-RAY IMAGING APPARATUS AND CONTROL METHOD THEREOF

CROSS-REFERENCE TO RELATED APPLICATION

This application claims the benefit of Korean Patent Application No. 10-2013-0067424, filed on Jun. 12, 2013 in the Korean Intellectual Property Office, the disclosure of which is incorporated herein by reference in its entirety.

BACKGROUND

1. Field

Exemplary embodiments of the present disclosure relate to an X-ray imaging apparatus and a control method thereof in which a clear 3D volume of an object may be acquired when the 3D volume of the object is reconstructed from X-ray images acquired by radiating X-rays to the object.

2. Description of the Related Art

In general, an X-ray imaging apparatus acquires an image of the inside of an object, such as a human body or an article, by radiating X-rays to the object. The X-ray imaging apparatus easily detects the internal structure of the object, and is thus used to detect abnormalities, such as lesions inside of a human body in a medical application, or to detect the internal structure of an article or a machine part. Further, the X-ray imaging apparatus may be used to check the inside of baggage in an airport.

Various types of X-ray imaging apparatuses are currently in use, including a digital radiography (DR) apparatus, a computed tomography (CT) apparatus, a full field digital mammography (FFDM) apparatus, etc.

Now, the operating principle of an X-ray imaging apparatus will be described. The X-ray imaging apparatus radiates X-rays to an object, such as a human body or an article, and then receives X-rays which are transmitted through the object or X-rays which are not transmitted through the object. The X-ray imaging apparatus converts the received X-rays into electrical signals, and reads out the converted electrical signals, thus generating X-ray images. The generated X-ray images are displayed through a display unit. Thereby, a user may detect the internal structure of the object.

SUMMARY

Therefore, it is an aspect of the exemplary embodiments to provide an X-ray imaging apparatus and a control method thereof in which a clear 3D volume of an object may be acquired when the 3D volume of the object is reconstructed from X-ray images acquired by radiating X-rays to the object.

Additional aspects of the exemplary embodiments will be set forth in part in the description which follows and, in part, will be obvious from the description, or may be learned by practice of the exemplary embodiments.

In accordance with an aspect of an exemplary embodiment, an X-ray imaging apparatus includes an image processing unit configured to acquire a plurality of X-ray images of an object from converted electrical signals, group the plurality of X-ray images into groups of X-ray images acquired from the same cardiac phase, and perform image reconstruction of each of the groups acquired as a result of the grouping.

In accordance with another aspect of an exemplary embodiment, a control method of an X-ray imaging apparatus includes radiating X-rays to an object from different positions using an X-ray generator, detecting X-rays transmitted through the object and converting the detected X-rays into electrical signals using an X-ray detector, acquiring a plurality of X-ray images of the object based on the converted electrical signals, grouping the plurality of X-ray images into groups of X-ray images acquired from the same cardiac phase, and performing image reconstruction of each of the groups acquired as a result of the grouping.

BRIEF DESCRIPTION OF THE DRAWINGS

These and/or other aspects of the exemplary embodiments will become apparent and more readily appreciated from the following description of the exemplary embodiments, taken in conjunction with the accompanying drawings of which:

FIG. 12 is a flowchart illustrating a control method of an X-ray imaging apparatus in accordance with an exemplary embodiment.

DETAILED DESCRIPTION

Figure 1:
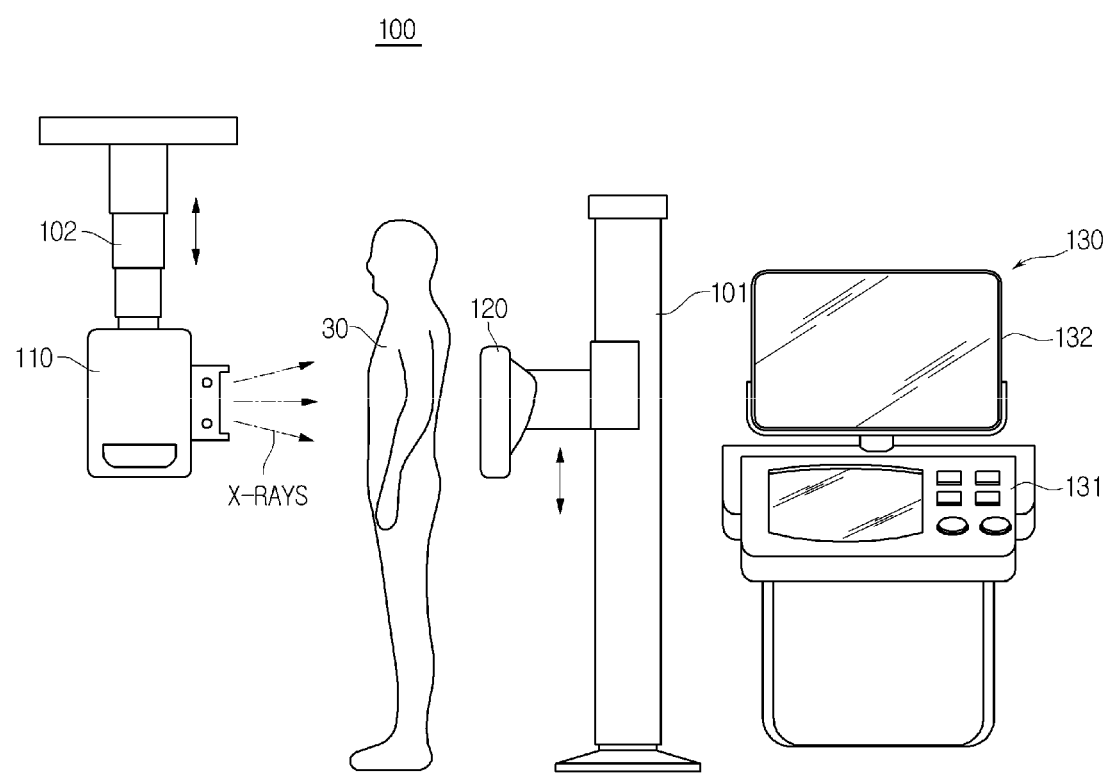
FIG. 1 is a perspective view of an X-ray imaging apparatus in accordance with an exemplary embodiment.

Reference will now be made in detail to the exemplary embodiments, examples of which are illustrated in the accompanying drawings, wherein like reference numerals refer to like elements throughout.

For exemplary purposes, an X-ray imaging apparatus described below according to an exemplary embodiment may be a tomosynthesis-type X-ray imaging apparatus. Tomosynthesis refers to radiation of X-rays to an object from different positions and acquisition of a plurality of X-ray images by detecting X-rays transmitted through the object. It is understood that exemplary embodiments are not limited to being implemented as a tomosynthesis-type X-ray imaging apparatus.

Types of tomosynthesis-type X-ray imaging apparatuses include a digital radiography (DR) apparatus and a computed tomography (CT) apparatus.

An X-ray imaging apparatus may be used to image various regions of a human body, for example, the chest, the oral cavity, the breast, and the bone. Hereinafter, an operation of the X-ray imaging apparatus if the X-ray imaging apparatus images the chest of a human body will be described in detail. For convenience of description, 'the chest of a human body' will be referred to as 'an object'.

FIG. 1 is a perspective view of an X-ray imaging apparatus 100 in accordance with an exemplary embodiment.

As exemplarily shown in FIG. 1, the X-ray imaging apparatus 100 may include an X-ray generator 110, an X-ray detector 120, and a host device 130.

The X-ray generator 110 is combined with a holder 102. The holder 102 is combined with rails provided on the ceiling. The holder 102 may move along the rails in the horizontal direction. By moving the holder 102 along the rails, the position of the X-ray generator 110 may move in the horizontal direction. Further, the length of the holder 102 may be adjusted in the upward and downward directions. Therefore, by adjusting the vertical length of the holder 102, the position of the X-ray generator 110 may move upwards and downwards.

The X-ray detector 120 is provided on a supporter 101. The X-ray detector 120 moves upwards and downwards along the supporter 101.

An object 30 is located between the X-ray generator 110 and the X-ray detector 120. When X-ray imaging is initiated, the X-ray generator 110 may move downwards or move upwards. According to an exemplary embodiment, movement of the X-ray generator 110 may be performed manually by an operator, or be performed automatically. For example, the operator may refer to a medical professional, such as a medical specialist or a doctor. As another example, the operator may refer to a person with qualifications equivalent to a medical professional, or authorized personnel. Broadly, the operator may refer to a user controlling an operation of the X-ray imaging apparatus 100.

The X-ray detector 120 may automatically move along with the X-ray generator 110. That is, during X-ray imaging, the X-ray generator 110 and the X-ray detector 120 may move downwards or upwards under the condition that the X-ray generator 110 and the X-ray detector 120 face each other with the object 30 located therebetween.

Although not shown in FIG. 1, the X-ray imaging apparatus 100 may further include a detection unit to detect the position of the X-ray generator 110. For example, the detection unit may be a camera. In this case, the camera may be installed around the supporter 101 or the X-ray detector 120 and image the X-ray generator 110. Then, the position of the X-ray generator 110 may be detected from an image acquired by the camera, and a moving distance of the X-ray detector 120 may be calculated based on a result of the detection. The X-ray detector 120 may move along with the X-ray generator 110 in such a manner.

Further, in order to more easily detect the position of the X-ray generator 110 from the image acquired by the camera, at least one marker may be provided on the X-ray generator 110. As one example, the at least one marker may have the same shape and/or color. As another example, the at least one marker may have different shapes and/or colors.

If the X-ray imaging apparatus 100 shown in FIG. 1 is used, X-ray images may be acquired by radiating X-rays to the object 30, which may be, for example, a person sitting down or standing.

The host device 130 may provide a user interface. The host device 130 may include an input unit 131 and a display unit 132.

The input unit 131 may receive instructions or a command to control operations of the X-ray imaging apparatus 100, input by an operator. The input unit 131 may include at least one of a foot pedal, a keyboard, and a mouse. The foot pedal may be provided at the lower portion of the host device 130. The keyboard may include at least one key and/or at least one knob.

The display unit 132 may display images acquired by the X-ray imaging apparatus 100. For example, the images acquired by the X-ray imaging apparatus 100 may be a plurality of X-ray images, 2D projection images, and 3D stereo images of the object 30. According to an exemplary embodiment, the 2D projection image refers to as an image acquired by performing volume rendering of 3D volume data, reconstructed from the plurality of X-ray images, based on a designated point of view. Further, the 3D stereo image refers to an image acquired by combining a left image and a right image respectively acquired by 3D volume data at a left point of view and a right point of view.

FIG. 1 illustrates the host device 130 as including one display unit 132. However, the exemplary embodiments are not limited thereto, and the host device 130 may include a plurality of display units 132. As one example, the host device 130 may include two display units 132. In this case, one display unit 132 may display a plurality of X-ray images, and the other display unit 132 may display 2D projection images or 3D stereo images.

As another example, the display area of the display unit 132 of the host device 130 may be divided into a plurality of sub-areas, and the respective sub-areas may display a plurality of X-ray images, 2D projection images, and 3D stereo images. Otherwise, during X-ray imaging, whenever the X-ray imaging apparatus 100 acquires an image, the display unit 132 may display the acquired image. At this time, the displayed image may be stored in a storage unit (not shown), or be displayed as an icon at the lower end of the display area.

The display method used to display each image through the display unit 132 may be set in advance by an operator. Further, the set values may be configured so as to be changeable by the operator during X-ray imaging or after completion of X-ray imaging.

Figure 2:
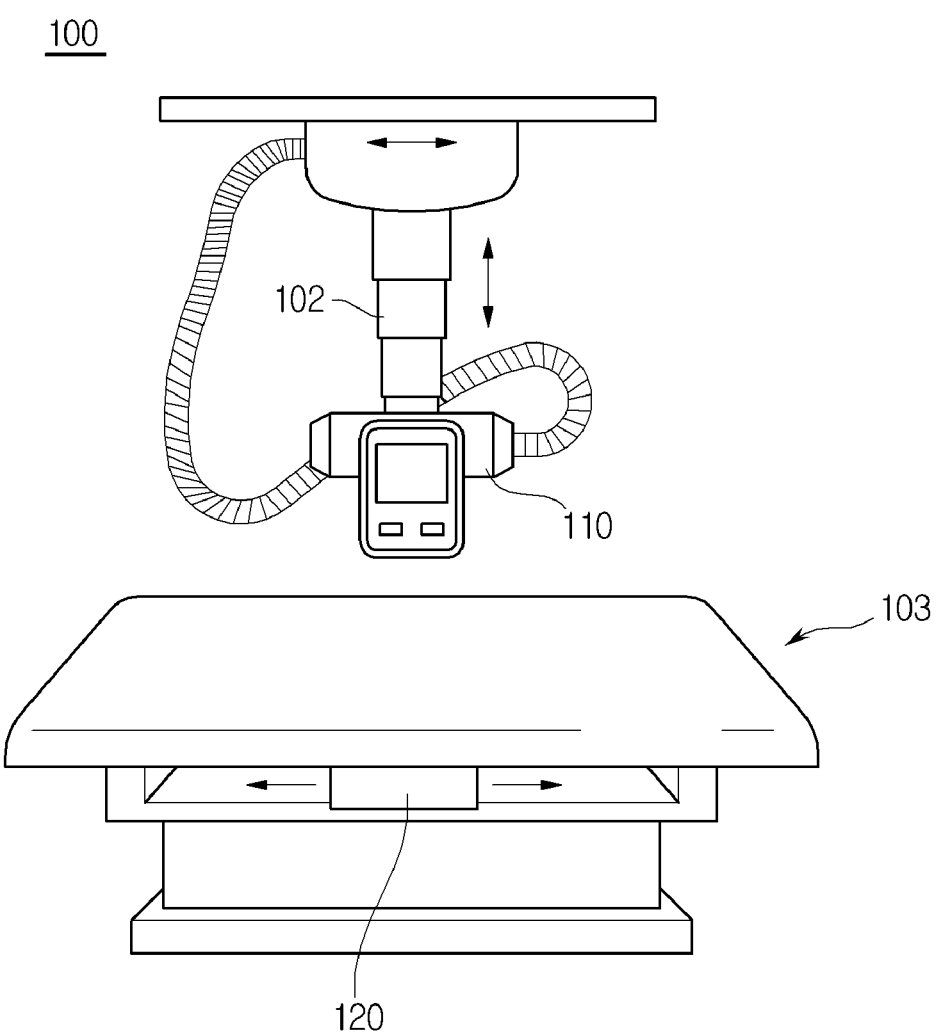
FIG. 2 is a perspective view of an X-ray imaging apparatus in accordance with another exemplary embodiment.

FIG. 2 is a perspective view of an X-ray imaging apparatus 100 in accordance with another exemplary embodiment.

The X-ray imaging apparatus 100 shown in FIG. 1 acquires X-ray images by radiating X-rays to the object 30, for example, a person sitting down or standing. In contrast, the X-ray imaging apparatus 100 shown in FIG. 2 acquires X-ray images by radiating X-rays to an object 30 placed on a table 103.

With reference to FIG. 2, the X-ray imaging apparatus 100 shown in FIG. 2 is substantially the same as the X-ray imaging apparatus 100 shown in FIG. 1 in that an X-ray generator 110 is combined with a holder 102 and the holder 102 moves along rails provided on the ceiling in the horizontal direction. The X-ray imaging apparatus 100 shown in FIG. 2 differs from the X-ray imaging apparatus 100 shown in FIG. 1 in that the table 103 is provided below the X-ray generator 110 of the X-ray imaging apparatus 100 shown in FIG. 2. An X-ray detector 120 is provided under the table 103. According to an exemplary embodiment, the X-ray detector 120 is installed under the table 103 so as to be movable in the horizontal direction.

When X-ray imaging is initiated, the X-ray generator 110 may move in the horizontal direction, for example, in the lengthwise direction of the table 103. According to an exemplary embodiment, movement of the X-ray generator 110 may be performed manually by an operator, or be performed automatically. The X-ray detector 120 may automatically move along with the X-ray generator 110. For this purpose, the X-ray imaging apparatus 100 may further include a detection unit (not shown) to detect the position of the X-ray generator 110.

Although FIG. 2 illustrates the X-ray generator 110 and the X-ray detector 120 as moving in the lengthwise direction of the table 103 (from left to right in FIG. 2), the X-ray generator 110 and the X-ray detector 120 may also move in the widthwise direction of the table 103 (from front to back in FIG. 2).

Figure 3:
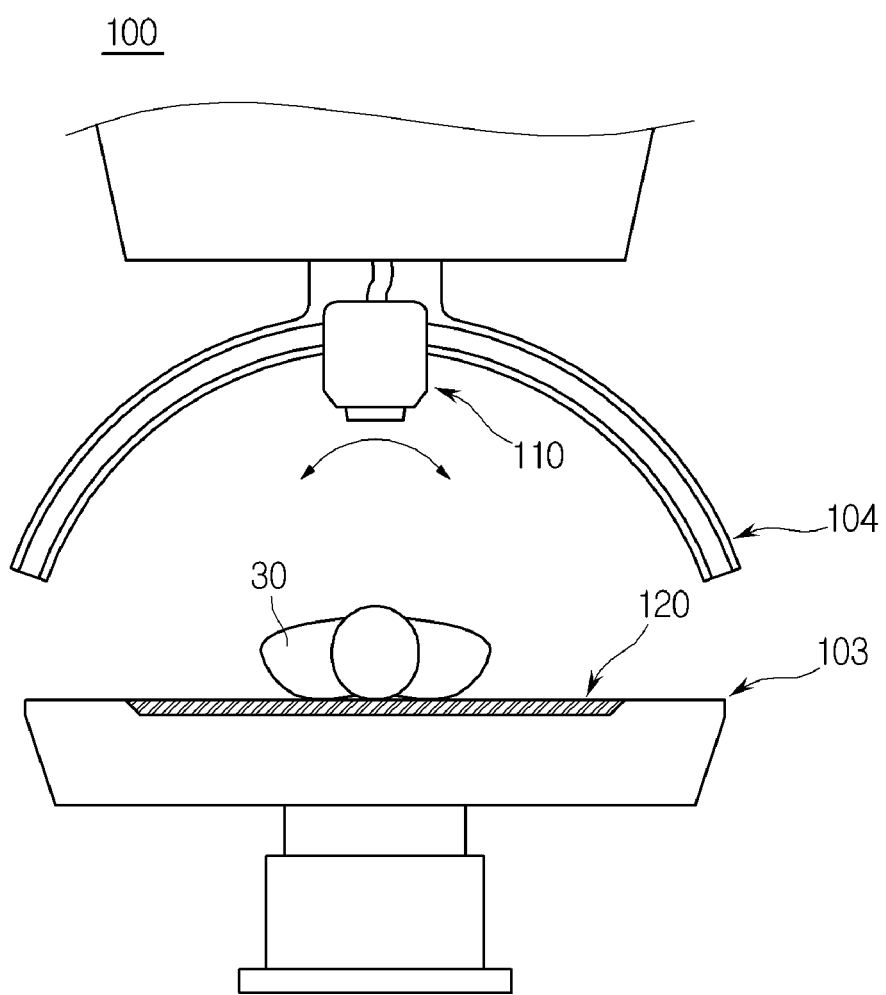
FIG. 3 is a perspective view of an X-ray imaging apparatus in accordance with another exemplary embodiment.

FIG. 3 is a perspective view of an X-ray imaging apparatus 100 in accordance with another exemplary embodiment.

The X-ray imaging apparatus 100 shown in FIG. 3 acquires X-ray images by radiating X-rays to an object 30 placed on a table 103, in the same manner as the X-ray imaging apparatus 100 shown in FIG. 2.

The X-ray imaging apparatus 100 shown in FIG. 3 is substantially the same as the X-ray imaging apparatus 100 shown in FIG. 2 in that the table 103 including an X-ray detector 120 is provided, but differs from the X-ray imaging apparatus 100 shown in FIG. 2 in that a C-arm 104 is provided in the X-ray imaging apparatus 100 shown in FIG. 3.

An X-ray generator 110 is provided on the C-arm 104. When X-ray imaging is initiated, the X-ray generator 110 moves along with the C-arm 104 and radiates X-rays to the object 30 from different positions. According to an exemplary embodiment, the position of the X-ray detector 120 provided on the table 103 may be fixed, although it is understood that the X-ray detector 120 may also be movable.

Although FIG. 3 illustrates the C-arm 104 having a position which is fixed and the X-ray generator 110 moving along the C-arm 104, alternatively, the position of the X-ray generator 110 may be fixed to the C-arm 104 and the C-arm 104 may move.

Figure 4:
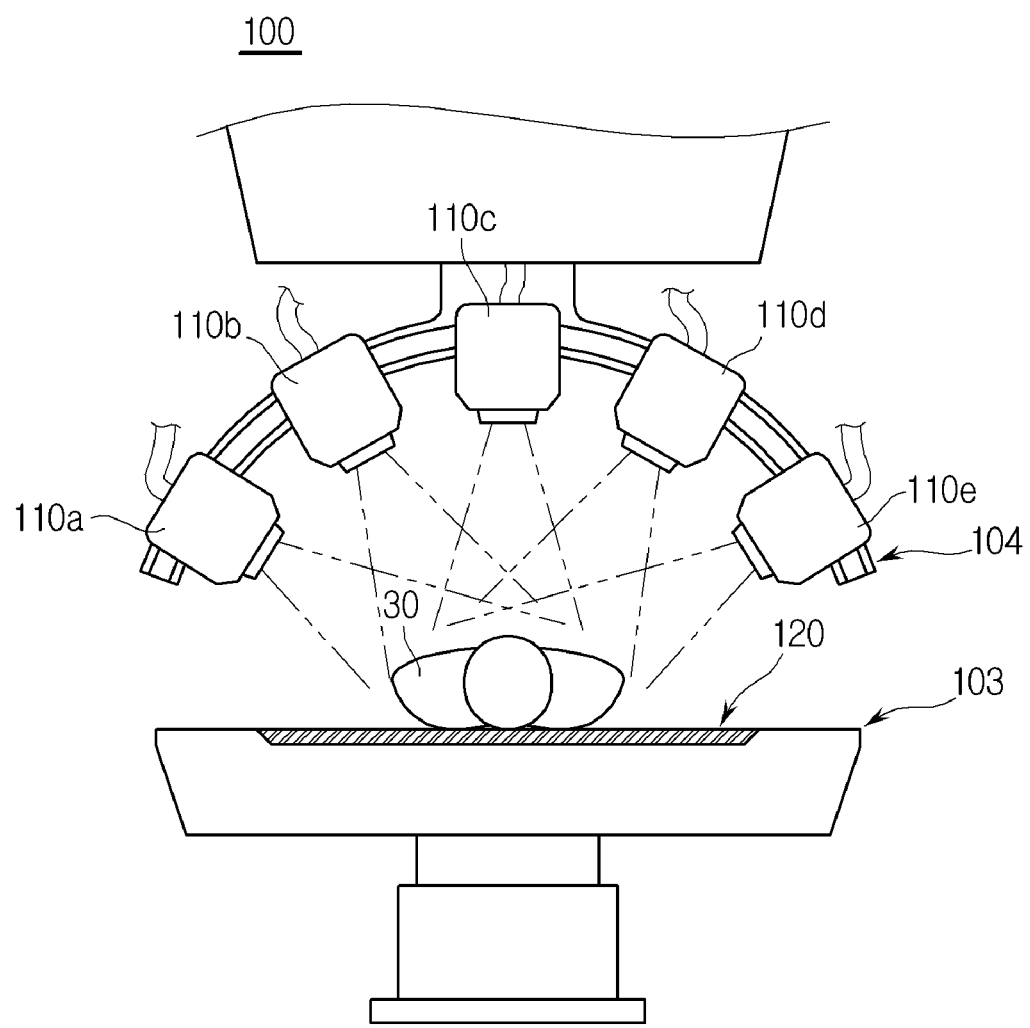
FIG. 4 is a perspective view of an X-ray imaging apparatus in accordance with a further exemplary embodiment.

FIG. 4 is a perspective view of an X-ray imaging apparatus 100 in accordance with a further exemplary embodiment.

The X-ray imaging apparatus 100 shown in FIG. 4 is substantially the same as the X-ray imaging apparatus 100 shown in FIG. 3 in that a C-arm 104 is provided, but differs from the X-ray imaging apparatus 100 shown in FIG. 3 in that a plurality of X-ray generators 110a, 110b, 110c, 110d, and 110e is provided on the C-arm 104 of the X-ray imaging apparatus 100 shown in FIG. 4.

When X-ray imaging is initiated, the plural X-ray generators 110a, 110b, 110c, 110d, and 110e may simultaneously radiate X-rays or sequentially radiate X-rays to an object 30. According to an exemplary embodiment, the position of an X-ray detector 120 provided on the table 103 may be fixed.

When the X-ray imaging apparatus 100 shown in FIG. 3 or the X-ray imaging apparatus 100 shown in FIG. 4 is used, X-rays are irradiated to the object 30 from different positions and thus, X-ray images may be acquired from different angles.

Although FIGS. 3 and 4 illustrate the X-ray detector 120 having a position which is fixed regardless of the position of the X-ray generator 110, the exemplary embodiments are not limited thereto. That is, the X-ray detector 120 may move along with the X-ray generator 110 so that the state in which the X-ray generator 110 and the X-ray detector 120 face each other may be maintained.

The X-ray imaging apparatuses 100 having different external appearances in accordance with various exemplary embodiments have been described above with reference to FIGS. 1 to 4. Hereinafter, control of an X-ray imaging apparatus 100 will be described.

Figure 5:
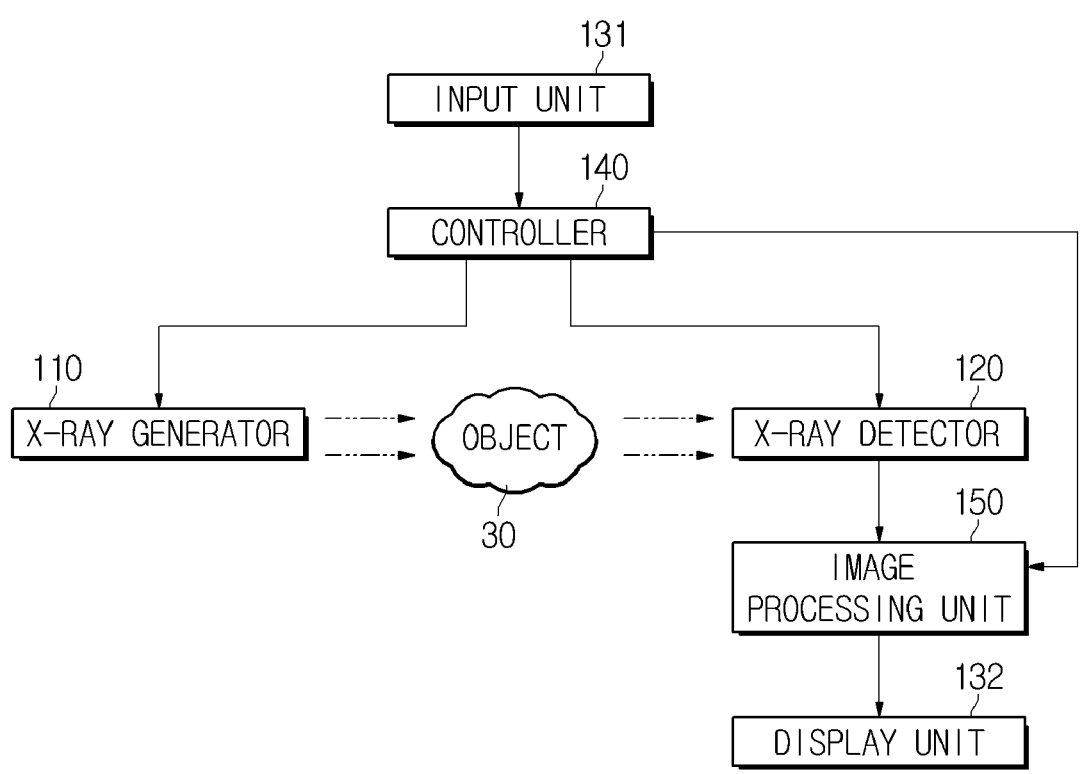
FIG. 5 is a control block diagram of an X-ray imaging apparatus according to an exemplary embodiment.

FIG. 5 is a control block diagram of the X-ray imaging apparatus 100 according to an exemplary embodiment.

As exemplarily shown in FIG. 5, the X-ray imaging apparatus 100 may include an input unit 131, a display unit 132, an X-ray generator 110, an X-ray detector 120, a controller 140, and an image processing unit 150.

The input unit 131 and the display unit 132 have been described above with reference to FIG. 1, and a detailed description thereof will thus be omitted.

The X-ray generator 110 generates X-rays and radiates the X-rays to an object 30. The X-ray generator 110 includes an X-ray tube 111 which generates X-rays. Hereinafter, a detailed description of the X-ray tube 111 will be given with reference to FIG. 6.

Figure 6:
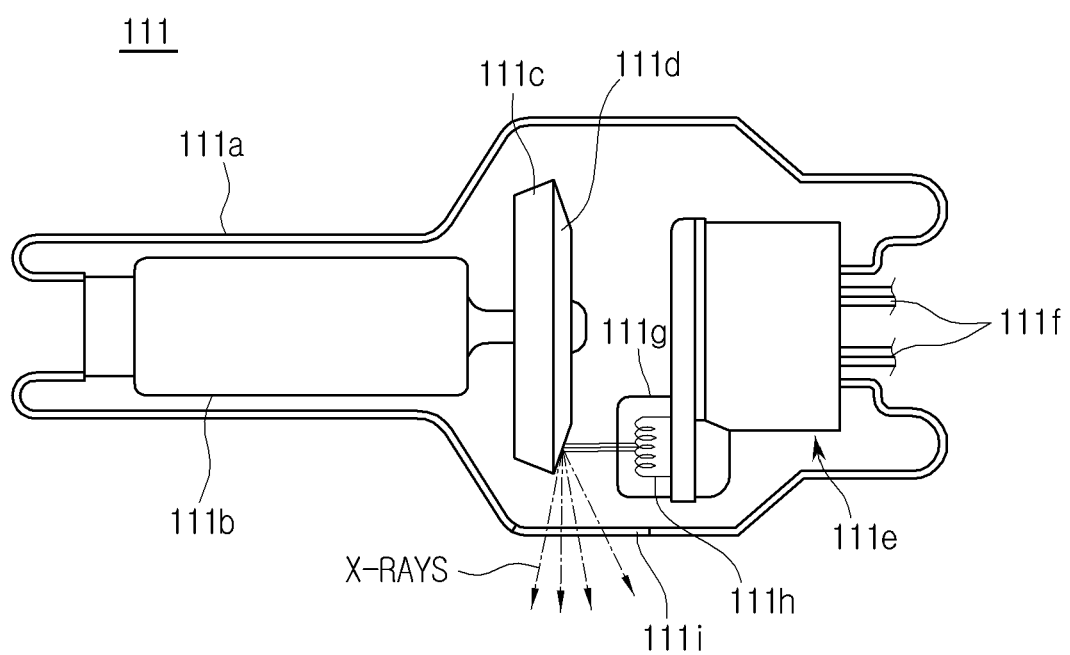
FIG. 6 is a cross-sectional view schematically illustrating the structure of an X-ray tube of an X-ray generator.

FIG. 6 is a cross-sectional view schematically illustrating the structure of the X-ray tube 111 of the X-ray generator 110.

With reference to FIG. 6, the X-ray tube 111 may be implemented as a diode vacuum tube including an anode 111c and a cathode 111e. As a tubular body, a glass tube 111a formed of hard silicate glass may be used, although is not limited thereto, and may alternatively be made of other materials, e.g., plastic, etc.

The cathode 111e includes a filament 111h and a focusing electrode 111g which focuses electrons. The focusing electrode 111g may be referred to as a focusing cup. A high vacuum state of about 10 mmHg is formed within the glass tube 111a and the filament 111h of the cathode 111e is heated to a high temperature, thus generating thermal electrons. For example, a tungsten filament may be used as the filament 111h and current may be applied to electric wires 111f connected to the filament 111h so as to heat the filament 111h. However, exemplary embodiments are not limited to implementing the filament 111h in the cathode 111e, and a carbon nano-tube which may be driven by a high speed pulse may be used as the cathode 111e.

The anode 111c is mainly formed of copper, and a target material 111d is applied to or disposed at a portion of the anode 111c facing the cathode 111e. For example, a high-Z material, for example, Cr, Fe, Co, Ni, W, or Mo, may be used as the target material 111d. As the melting point of the target material 111d becomes higher, a focal spot size is correspondingly reduced.

When high voltage is applied between the cathode 111e and the anode 111c, thermal electrons are accelerated and collide with the target material 111d of the anode 111c, thus generating X-rays. The generated X-rays are radiated to the outside through a window 111i. The window 111i may be formed of a beryllium (Be) thin film. A filter (not shown) may be located on the front or rear surface of the window 111i to filter out X-rays of a specific energy band.

The target material 111d may be rotated by a rotor 111b. When the target material 111d is rotated, a thermal accumulation rate may increase 10 times or more and the focal spot size may be reduced, as compared to a case in which the target material 111d is fixed.

Voltage applied between the cathode 111e and the anode 111c of the X-ray tube 111 is referred to as tube voltage. The intensity of the tube voltage may be expressed as a peak value (unit: kVp).

As tube voltage increases, the velocity of thermal electrons increases. As a result, the energy of X-rays generated by collision of the thermal electrons with the target material 111d (the energy of photons) increases. When the energy of the X-rays increases, the amount of the X-rays transmitted through the object 30 increases. When the transmission amount of the X-rays increases, the amount of X-rays detected by the X-ray detector 120 increases. Consequently, an X-ray image having a high signal to noise ratio (SNR), e.g., a high quality X-ray image, is acquired.

On the other hand, as tube voltage decreases, the velocity of thermal electrons decreases and the energy of X-rays generated by collision of the thermal electrons with the target material 111d decreases. When the energy of X-rays decreases, the amount of X-rays absorbed by the object 30 increases and the amount of X-rays detected by the X-ray detector 120 decreases. Consequently, an X-ray image having a low SNR, e.g., a low quality X-ray image, is acquired.

Current flowing in the X-ray tube 111 is referred to as tube current, and the intensity of tube current may be expressed as mean amperage (unit: mA). As tube current increases, the amount of X-rays (the number of photons: X-ray dose) increases and an X-ray image having a high SNR is acquired. On the other hand, as tube current decreases, the amount of X-rays decreases and an X-ray image having a low SNR is acquired.

In summary, the energy of X-rays may be controlled by adjusting tube voltage. Further, the dose or intensity of X-rays may be controlled by adjusting tube current and X-ray exposure time. Therefore, the energy or dose of radiated X-rays may be controlled by controlling tube voltage or tube current according to kind and characteristics of the object 30.

X-rays radiated from the X-ray generator 110 have a constant energy band. The energy band may be defined by an upper limit and a lower limit. The upper limit of the energy band, e.g., the maximum energy of radiated X-rays, may be adjusted by the intensity of tube voltage. The lower limit of the energy band, e.g., the minimum energy of radiated X-rays, may be adjusted by a filter (not shown) provided on the X-ray generator 110. When the filter filters out X-rays of a lower energy band, the mean energy of the radiated X-rays may be increased. Further, the energy of the radiated X-rays may be expressed as the maximum energy or the mean energy.

Referring to FIG. 5 again, the X-ray detector 120 detects X-rays transmitted through the object 30 and converts the X-rays into electrical signals. Hereinafter, a more detailed description of the X-ray detector 120 will be given with reference to FIG. 7.

Figure 7:
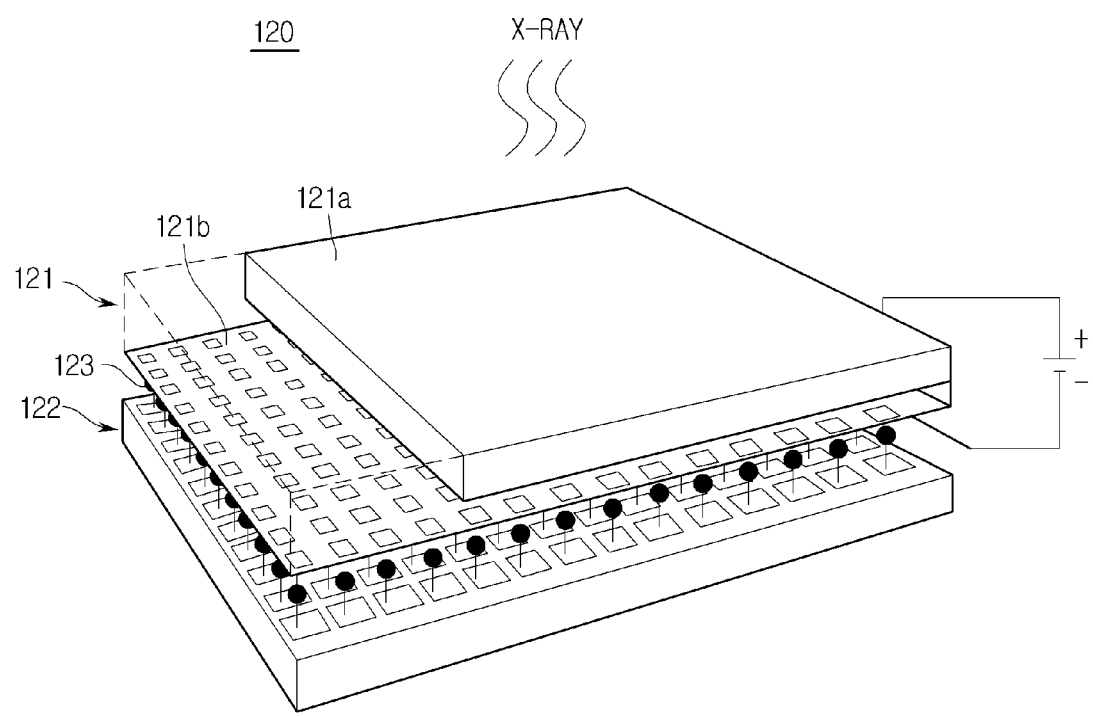
FIG. 7 is a view schematically illustrating the structure of an X-ray detector.

With reference to FIG. 7, the X-ray detector 120 includes a light receiving element 121 which detects X-rays and converts the detected X-rays to electrical signals, and a readout circuit 122 which reads the electrical signals. According to an exemplary embodiment, the readout circuit 122 is formed in a 2D pixel array structure including a plurality of pixel areas. The light receiving element 121 may be formed of a single crystal semiconductor material. For example, the single crystal semiconductor material may include at least one of Ge, CdTe, CdZnTe, and GaAs. When the single crystal semiconductor material is used, high resolution, rapid response time, and a high dynamic area may be assured at a low energy and a low dose.

The light receiving element 121 may be a PIN photo diode formed by bonding a p-type layer 121b, in which a p-type semiconductor is arranged in a 2D pixel array structure, to the lower surface of a high-resistance n-type semiconductor substrate 121a. The readout circuit 122 formed using a CMOS process is combined with the light receiving element 121 at respective pixels. The CMOS readout circuit 122 and the light receiving element 121 may be bonded through a flip chip bonding method. In more detail, the CMOS readout circuit 122 and the light receiving element 121 may be bonded using bumps 123 formed of solder (PbSn) or indium (In) through reflow and thermocompression. It is understood that the above-described structure is only one example of the X-ray detector 120 and the structure of the X-ray detector 120 is not limited thereto.

Referring to FIG. 5 again, the controller 140 may connect the respective elements of the X-ray imaging apparatus 100 and control the respective elements. For example, the controller 140 may control movement of the position(s) of the X-ray generator 110 and/or the X-ray detector 120. In more detail, the controller 140 may locate the X-ray generator 110 and the X-ray detector 120 at initial positions and then move the X-ray generator 110 and the X-ray detector 120 so as to maintain a state in which the X-ray generator 110 and the X-ray detector 120 face each other. If the position of the X-ray generator 110 is moved manually by an operator, the controller 140 may move the X-ray detector 120 along with the X-ray generator 110.

The image processing unit 150 may generate X-ray images based on electrical signals output from the respective pixels of the X-ray detector 120. As described above, the X-ray generator 110 radiates X-rays to the object 30 from different positions. Therefore, the image processing unit 150 may generate X-ray images corresponding to the respective positions of the X-ray generator 110. When a plurality of X-ray images is acquired, the image processing unit 150 may group the plurality of X-ray images depending on a designated criterion and perform image reconstruction of each group among a plurality of groups. Hereinafter, a more detailed description of the image processing unit 150 will be given with reference to FIG. 8.

Figure 8:
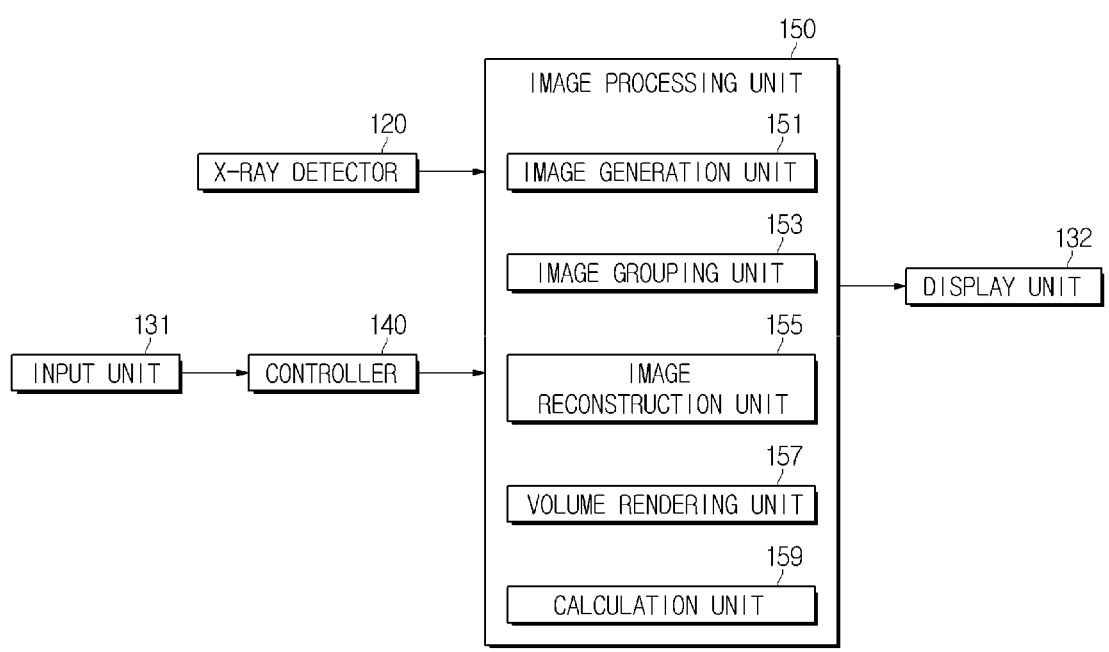
FIG. 8 is a view illustrating an image processing unit in detail.

As exemplarily shown in FIG. 8, the image processing unit 150 includes an image generation unit 151, an image grouping unit 153, an image reconstruction unit 155, a volume rendering unit 157, and a calculation unit 159.

The image generation unit 151 may generate X-ray images based on electrical signals output from the respective pixels of the X-ray detectors 120. In more detail, whenever the X-ray generator 110 radiates X-rays to the object 30 from different positions, the respective pixels of the X-ray detector 120 may output electrical signals, and the image generation unit 151 may generate a plurality of X-ray images based on the electrical signals.

The plural X-ray images may be stored in a storage unit (not shown), or be provided to the image grouping unit 153 which will be described later. According to an exemplary embodiment, the storage unit may be implemented as one of a volatile memory device, a nonvolatile memory device, a hard disc, an optical disc, and combinations thereof. However, the storage unit is not limited thereto and may be implemented as any of the storage devices known in the art.

The image grouping unit 153 may group the plural X-ray images provided from the image generation unit 151 or the plural X-ray images stored in the storage unit depending on a designated criterion.

Specifically, the heart located within the chest of a human body consists of two atria and two ventricles. The heart beats in a designated cycle, and a period from one heart beat to the next heart beat is referred to as a cardiac cycle. A single cardiac cycle may be divided into an atrial systolic phase, a ventricular systolic phase, and an atrial and ventricular diastolic phase. In the atrial systolic phase, the left atrium and the right atrium contract and the left ventricle and the right ventricle relax. In the ventricular systolic phase, the left atrium and the right atrium relax and the left ventricle and the right ventricle contract. In the atrial and ventricular diastolic phase, the left atrium, the right atrium, the left ventricle, and the right ventricle relax.

Since the heart is always beating, if X-rays are radiated to the object 30 from different positions, a plurality of X-ray images in different cardiac phases is acquired. When image reconstruction is performed based on the plural X-ray images acquired from different cardiac phases, 3D volume data in which an area around the heart is blurred is acquired. Therefore, according to an exemplary embodiment, in order to prevent degradation of the quality of 3D volume data, the plural X-ray images acquired from different cardiac phases are grouped into X-ray images acquired from the same cardiac phase.

Therefore, according to an exemplary embodiment, grouping the plural X-ray images depending on a designated criterion through the image grouping unit 153 refers to a technique of grouping the plural X-ray images into X-ray images acquired from the same cardiac phase. For this purpose, the image grouping unit 153 may detect characteristics from the plural X-ray images and group the plural X-ray images based on the detected characteristics.

As one example, the image grouping unit 153 may detect a cardiac area from the plural X-ray images and group the plural X-ray images into X-ray images having the cardiac area of the same shape. As the heart repeatedly contracts and relaxes, as described above, the overall shape of the heart varies. Therefore, when the cardiac area is detected from designated X-ray images, if the shapes of the detected cardiac area are the same, it may be understood that the corresponding X-ray images have been acquired from the same cardiac phase.

As another example, the image grouping unit 153 may detect a cardiac area from the plural X-ray images and calculate a brightness distribution histogram of the detected cardiac area. Thereafter, the image grouping unit 153 may group the plural X-ray images into X-ray images having the same brightness distribution of the cardiac area based on a result of calculation.

As another example, the image grouping unit 153 may detect boundaries of an atrium (for example, the left atrium) from the plural X-ray images and calculate position information of the detected boundaries of the atrium. Then, the image grouping unit 153 may group the plural X-ray images into X-ray images having the same calculated position information of the detected boundaries of the atrium. As the heart repeatedly contracts and relaxes, the position of the boundary of the atria varies. Therefore, when the boundaries of the atrium are detected from designated X-ray images and position information of the detected boundaries of the atrium are calculated, if the calculated position information of the detected boundaries of the atrium are substantially the same, it may be understood that the corresponding X-ray images have been acquired from the same cardiac phase.

As another example, the image grouping unit 153 may detect boundaries of a blood vessel connected to the heart (for example, the aorta) from the plural X-ray images and calculate position information of the detected boundaries of the blood vessel. Then, the image grouping unit 153 may group the plural X-ray images into X-ray images having substantially the same calculated position information of the detected boundaries of the blood vessel. As the heart repeatedly contracts and relaxes, the position of the boundary of the blood vessel connected to the heart varies. Therefore, when the boundaries of the blood vessel are detected from designated X-ray images and position information of the detected boundaries of the blood vessel are calculated, if the calculated position information of the detected boundaries of the blood vessel are substantially the same, it may be understood that the corresponding X-ray images have been acquired from the same cardiac phase.

As another example, the image grouping unit 153 may detect a blood vessel connected to the heart (for example, the aorta) respectively from the plural X-ray images and calculate the widths of the detected blood vessel. Then, the image grouping unit 153 may group the plural X-ray images into X-ray images having the same calculated width of the blood vessel. When the left atrium contracts, blood in the left atrium is discharged to the aorta, and thereby, the width of the aorta varies. Therefore, when the blood vessel is detected from designated X-ray images and the widths of the blood vessel are calculated, if the calculated widths of the blood vessel are the same, it may be understood that the corresponding X-ray images have been acquired from the same cardiac phase.

As a further example, the image grouping unit 153 may detect a blood vessel area connected to the heart from the plural X-ray images and calculate a brightness distribution histogram of the detected blood vessel area. Thereafter, the image grouping unit 153 may group the plural X-ray images into X-ray images having the same brightness distribution of the blood vessel area based on a result of calculation.

As described above, the image grouping unit 153 may group a plurality of X-ray images using one of many different types of criteria related to a cardiac cycle, such as, for example, the shape of the cardiac area, the brightness distribution of the cardiac area, the position information of the boundary of the atrium, the position information of the boundary of the blood vessel, the width of the blood vessel, and the brightness distribution of the blood vessel area. In accordance with another exemplary embodiment, the image grouping unit 153 may group a plurality of X-ray images using at least two of the above-described characteristics. The characteristics among the above characteristics which are used to group the plural X-ray images may be set in advance by an operator. The X-ray images classified into a plurality of groups by the predetermined criterion may be displayed by the display unit 132. It is understood that the above criteria are exemplary only, and that exemplary embodiments may utilize many other types of criteria related to a cardiac cycle.

The image reconstruction unit 155 may perform image reconstruction of each of the respective groups. As one example, the image reconstruction unit 155 may perform image reconstruction of all groups. As another example, the image reconstruction unit 155 may select at least one group from among a plurality of groups according to instruction or a command input by an operator, and perform image reconstruction of the at least one selected group. Hereinafter, image reconstruction will be described briefly.

According to an exemplary embodiment, image reconstruction refers to a technique of reconstructing an object represented in 2-dimensional X-ray images to a 3D image that looks similar to a real object. Image reconstruction may be performed through various methods, such as an iterative method, a non-iterative method, a direct Fourier method, and a back projection method.

In the iterative method, X-ray images (projection data) are continuously compensated for until data close to the original structure of the object 30 is acquired. In the non-iterative method, the object 30 which is 2-dimensionally expressed is reconstructed into a 3D image by applying an inverse conversion function of a conversion function, used in modeling of the 3D object 30 into 2D images, to a plurality of X-ray images. As one example of the non-iterative method, filtered back projection may be used. In filtered back projection, in order to offset blur around the central regions of X-ray images, filtering is carried out and then, back projection is carried out. In the direct Fourier method, X-ray images are converted from a spatial domain to a frequency domain. In the back projection method, X-ray images acquired at a plurality of points of view are returned to one screen.

The image reconstruction unit 155 may perform image reconstruction of each group of respective groups using one of the above-described methods. When image reconstruction of each of the respective groups is performed, 3D volume data of each of the respective groups may be acquired. The 3D volume data may be expressed as a plurality of voxels. It may be understood that a pixel defines one point in a 2D plane and a voxel defines one point in a 3D space. The pixel includes x and y coordinates, and a voxel includes x, y, and z coordinates.

Figure 9:
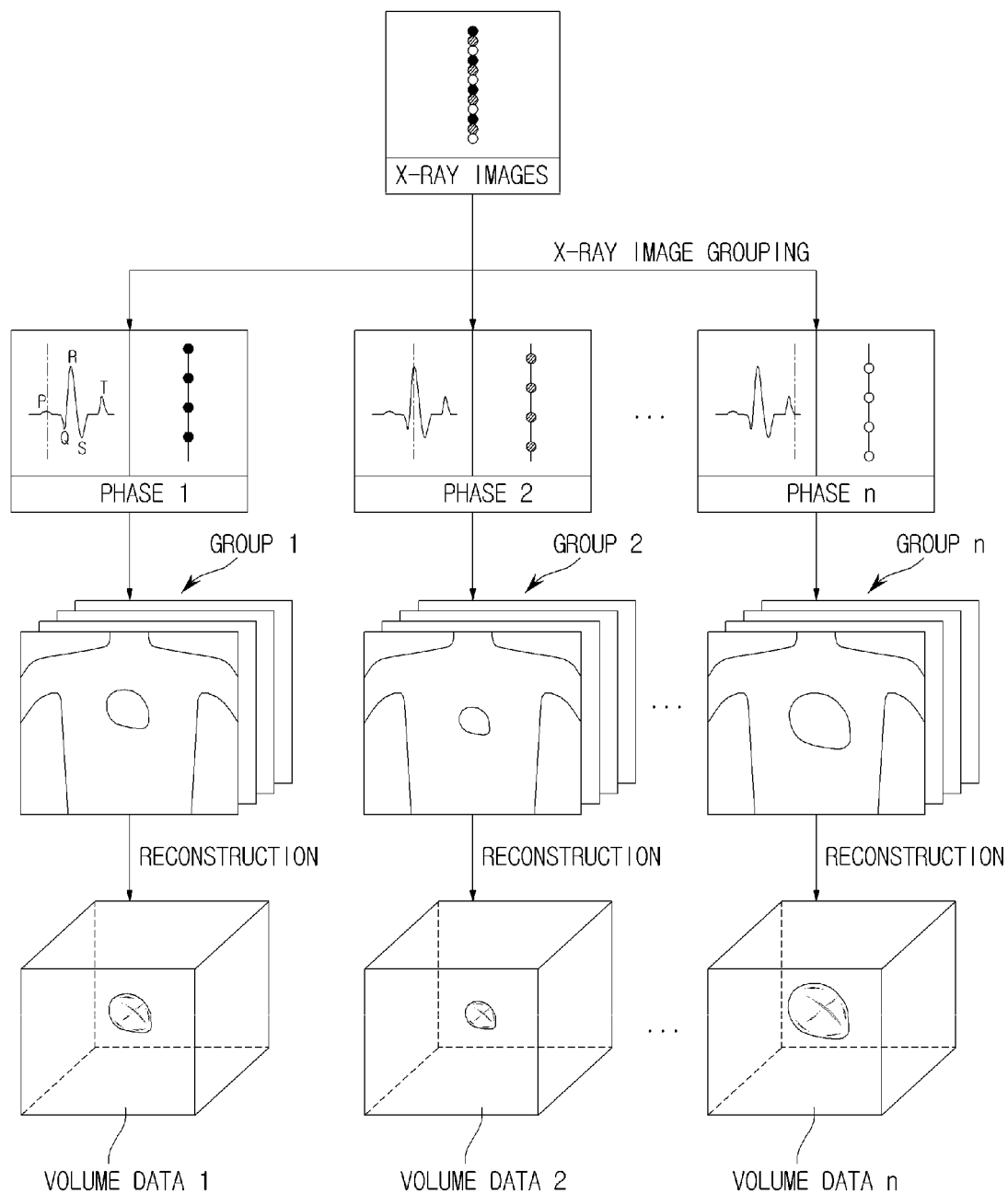
FIG. 9 is a view illustrating a process of acquiring 3D volume data of each group among groups from a plurality of X-ray images acquired by the X-ray imaging apparatus of FIG. 1 or 2.

FIG. 9 is a view illustrating a process of acquiring 3D volume data of each group of groups from a plurality of X-ray images acquired by the X-ray imaging apparatus 100 of FIG. 1 or 2.

In the X-ray imaging apparatus 100 of FIG. 1 or 2, as the X-ray generator 110 and the X-ray detector 120 facing the X-ray generator 110 move in the upward and downward directions with the object 30 located therebetween, a plurality of X-ray images of the object 30 is acquired.

When the plurality of X-ray images is acquired, the image grouping unit 153 detects characteristics from the respective X-ray images. Then, the image grouping unit 153 groups the plural X-ray images into X-ray images acquired from the same cardiac phase based on the detected characteristics. For example, with reference to an electrocardiogram (ECG) waveform shown in FIG. 9, the image grouping unit 153 may group the plural X-ray images into X-ray images corresponding to P waves of the ECG waveform, X-ray images corresponding to QRS waves, and X-ray images corresponding to T waves. The ECG waveform shown in FIG. 9 is provided only to aid in understanding of X-ray image grouping, and X-ray image grouping is not required to be performed based on the ECG waveform. X-ray image grouping may be performed based on characteristics detected from the respective X-ray images.

FIG. 9 illustrates grouping of X-ray images into n groups. When X-ray image grouping has been completed, the image reconstruction unit 155 performs image reconstruction of each of at least one group selected from among the plural groups. According to an exemplary embodiment, group selection may be carried out by instructions or a command of an operator. When the X-ray images classified according to groups are displayed through the display unit 132, the operator may select at least one group from the displayed groups. If the operator does not select a group, the image reconstruction unit 155 may, for example, perform image reconstruction upon all of the groups or a designated subset of all of the groups.

When image reconstruction of each of the groups is performed, 3D volume data of each of the groups may be acquired. With reference to FIG. 9, n sets of 3D volume data (volume data 1, volume data 2, . . . , volume data n) corresponding to n groups (group 1, group 2, . . . , group n) are acquired. The 3D volume data acquired in such a manner clearly displays an area around the heart, as compared to 3D volume data acquired by performing image reconstruction without grouping a plurality of X-ray images.

Figure 10:
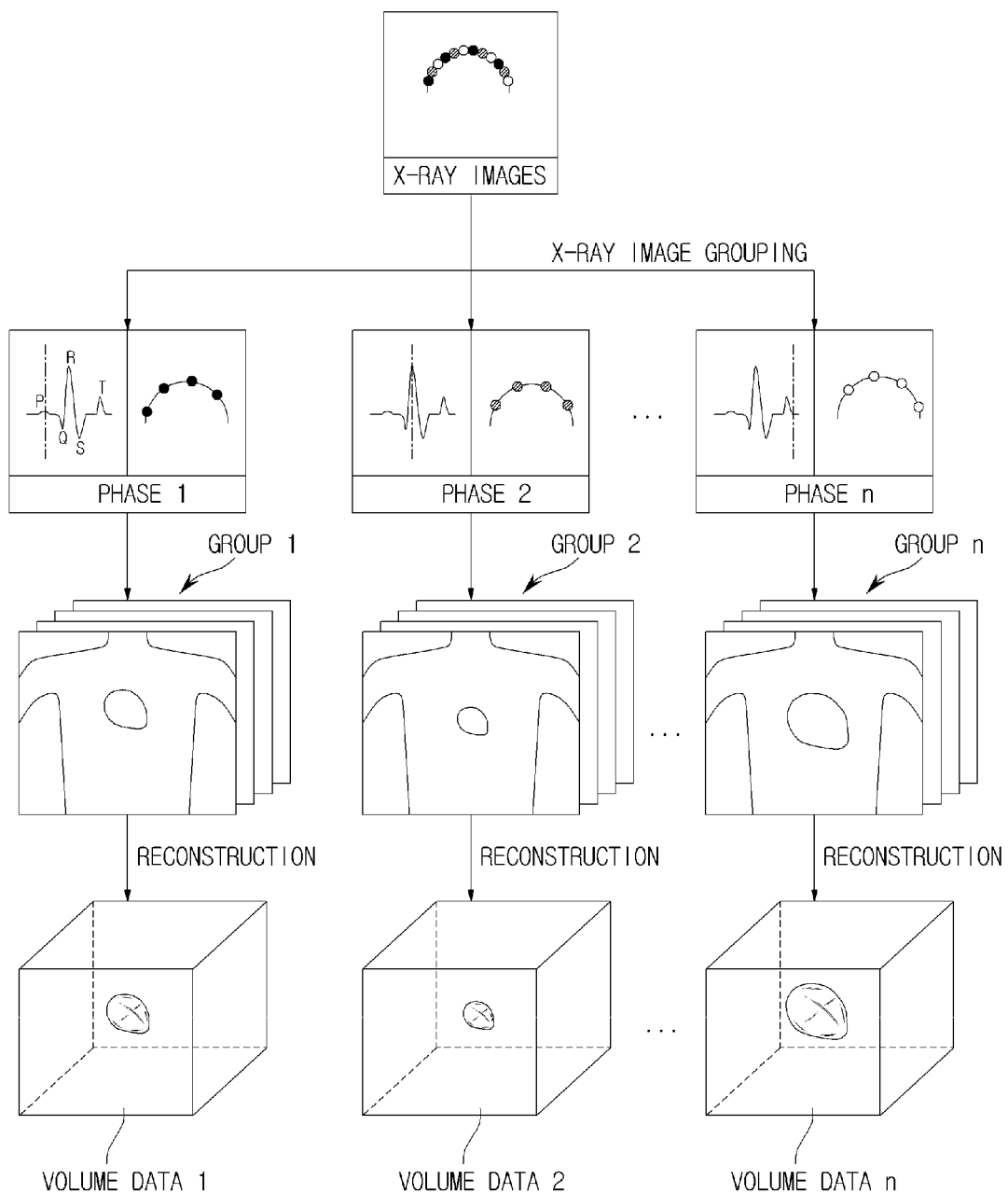
FIG. 10 is a view illustrating a process of acquiring 3D volume data of each group among groups from a plurality of X-ray images acquired by the X-ray imaging apparatus of FIG. 3 or 4.

FIG. 10 is a view illustrating a process of acquiring 3D volume data of each group of groups from a plurality of X-ray images acquired by the X-ray imaging apparatus 100 of FIG. 3 or 4.

The X-ray imaging apparatus 100 of FIG. 3 or 4 radiates X-rays to an object 30 from different angles, and thus acquires a plurality of X-ray images of the object 30.

When the plurality of X-ray images is acquired, the image grouping unit 153 detects characteristics from the respective X-ray images. Then, the image grouping unit 153 groups the plural X-ray images into X-ray images acquired from the same cardiac phase based on the detected characteristics. For example, the image grouping unit 153 may group the plural X-ray images into X-ray images corresponding to P waves of the ECG waveform shown in FIG. 10, X-ray images corresponding to QRS waves, and X-ray images corresponding to T waves. FIG. 10 illustrates grouping of X-ray images into n groups. The ECG waveform shown in FIG. 10 is provided only to aid in understanding of X-ray image grouping, and X-ray image grouping is not necessarily performed based on the ECG waveforms. X-ray image grouping may be performed based on characteristics detected from the respective X-ray images.

When X-ray image grouping has been completed, the image reconstruction unit 155 performs image reconstruction of each of at least one group selected from among the plural groups. According to an exemplary embodiment, group selection may be carried out by instructions or a command of an operator. If the operator does not select a group, the image reconstruction unit 155 may, for example, perform image reconstruction upon all of the groups or a designated subset of all of the groups.

When image reconstruction of each of the groups is performed, 3D volume data of each of the groups may be acquired. With reference to FIG. 10, n sets of 3D volume data (volume data 1, volume data 2, . . . , volume data n) corresponding to n groups (group 1, group 2, . . . , group n) are acquired. The 3D volume data acquired in such a manner clearly displays an area around the heart, as compared to 3D volume data acquired by performing image reconstruction without grouping a plurality of X-ray images.

Referring to FIG. 8 again, the volume rendering unit 157 may perform volume rendering of each set of the respective sets of volume data. Volume rendering refers to a projection of 3D volume data onto a 2D plane based on a designated point of view. Volume rendering may be divided into surface rendering and direct volume rendering.

Surface rendering is a technique which includes extracting surface information from volume data based on predetermined scalar values and amounts of spatial changes, converting the surface information into a geometric factor, such as a polygon or a curved patch, and then applying a conventional rendering technique to the geometric factor. Examples of the surface rendering include a marching cubes algorithm and a dividing cubes algorithm.

Direct volume rendering is a technique which includes directly rendering volume data without converting volume data into a geometric factor. Direct volume rendering is useful to represent a translucent structure since direct volume rendering can visualize the inside of an object accurately. The direct volume rendering may be classified into an object-order method and an image-order method according to a process of approaching volume data.

The object-order method includes searching for volume data in its storage order and synthesizing each voxel with the corresponding pixel. A representative example of the object-order method is splatting.

The image-order method includes sequentially deciding pixel values in the order of scan lines of an image. Examples of the image-order method include Ray-Casting and Ray-Tracing.

Figure 11:
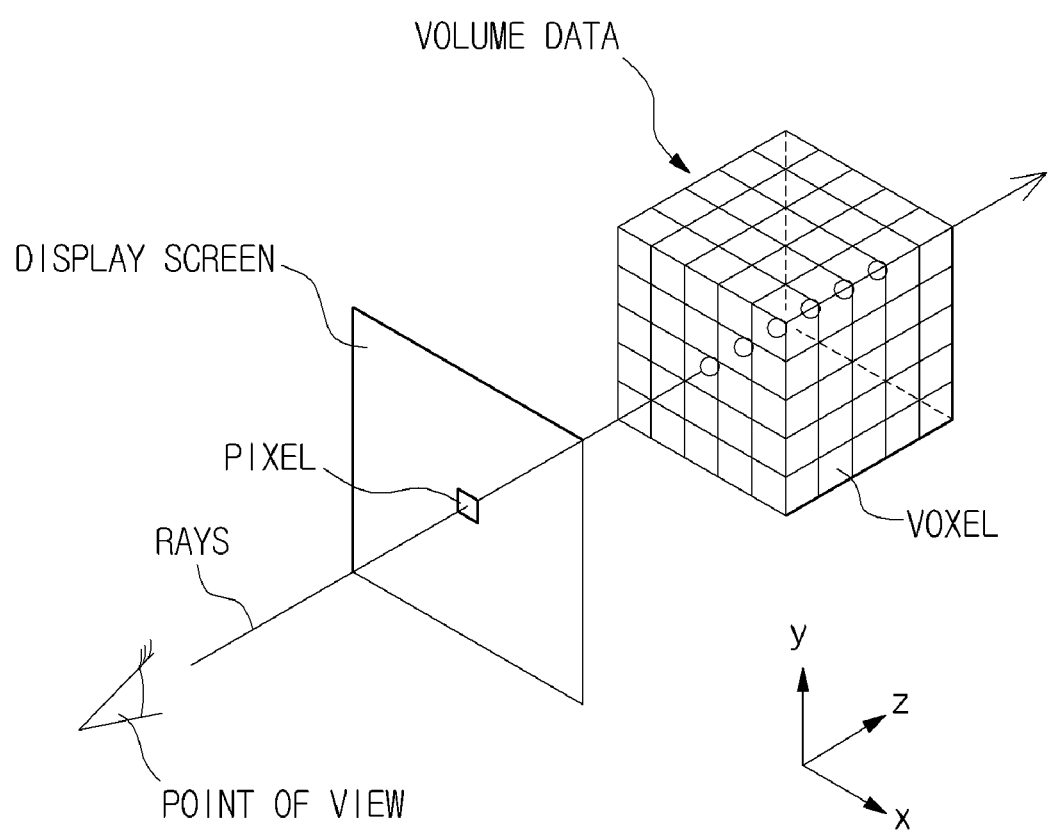
FIG. 11 is a view illustrating volume rendering.

In ray-casting, as exemplarily shown in FIG. 11, virtual rays are radiated from a point of view toward a designated pixel of a display screen. Thereafter, voxels through which such rays pass are detected from voxels of volume data. Then, a brightness value of the corresponding pixel of the display screen is determined by accumulating brightness values of the detected voxels. Alternatively, the mean value of the detected voxels may be determined as the brightness value of the corresponding pixel. As another alternative, the weighted mean value of the detected voxels may be determined as the brightness value of the corresponding pixel.

Ray-tracing refers to a method in which paths of rays reaching eyes of an observer are traced one by one. In contrast to ray-casting, in which only intersection points of rays with volume data are detected, ray-tracing may simulate reflection and refraction of radiated rays by tracing the radiated rays.

Ray-tracing may be divided into forward ray-tracing and backward ray-tracing. Forward ray-tracing is a technique in which rays ultimately reaching eyes of an observer are detected by modeling reflection, scattering, and transmission of rays radiated from a virtual light source due to contact with volume data. Backward ray-tracing is a technique in which paths of rays reaching eyes of an observer are traced in the backward direction.

Referring to FIG. 8 again, the volume rendering unit 157 may perform volume rendering of each set of 3D volume data using one of the above-described volume rendering techniques. According to an exemplary embodiment, the volume rendering unit 157 may perform volume rendering of each set of the 3D volume data at the same point of view.

When volume rendering of 3D volume data at one point of view is performed, a 2D projection image may be acquired. Therefore, when volume rendering of all sets of 3D volume data has been completed, a plurality of 2D projection images may be acquired.

If volume rendering of 3D volume data at two points of view corresponding to the left and right eyes of a human is performed, a left image and a right image may be acquired. When two images are combined, a 3D stereo image may be acquired. When volume rendering of all sets of 3D volume data is performed using the same method, a plurality of 3D stereo images may be acquired.

The plural 2D projection images or the plural 3D stereo images acquired as a result of volume rendering may be displayed by the display unit 132. Specifically, the plural 2D projection images may be sequentially displayed by the display unit 132. When the plural 2D projection images are sequentially displayed, an operator may confirm a motion of the heart. Moreover, since a clear image around the heart is displayed, an error in diagnosis may be reduced.

The calculation unit 159 may calculate a cardiac output based on the acquired 3D volume data of each of the groups. Specifically, the calculation unit 159 may calculate the volumes of the heart from the 3D volume data of each of the groups. Thereafter, the calculation unit 159 may calculate a cardiac output by calculating a difference between the maximum value and the minimum value of the calculated volumes of the heart. As one example, a calculation of the cardiac output may be performed if instructions or a command of an operator are input through the input unit. As another example, a calculation of the cardiac output may be automatically performed without input of instructions or a command of an operator.

FIG. 12 is a flowchart illustrating a control method of an X-ray imaging apparatus 100 in accordance with an exemplary embodiment.

First, X-rays are radiated to the object 30 from different positions at Operation S500, and thus, a plurality of X-ray images are acquired at Operation S510.

Thereafter, the plural X-ray images are grouped according to heart phases at Operation S520. That is, the plural X-ray images are grouped into X-ray images acquired from the same heart phase. Operation S520 may include detecting characteristics of the plural X-ray images depending on a predetermined criterion, and grouping the plural X-ray images based on the detected characteristics.

As one example, a cardiac area may be detected from the plural X-ray images, and the plural X-ray images may be grouped into X-ray images having the same shape of the cardiac area.

As another example, a cardiac area may be detected from the plural X-ray images, a brightness distribution histogram of the detected cardiac area may be calculated, and the plural X-ray images may be grouped into X-ray images having the same brightness distribution of the cardiac area based on a result of calculation.

As another example, boundaries of an atrium may be detected from the plural X-ray images, position information of the detected boundaries of the atrium may be calculated, and the plural X-ray images may be grouped into X-ray images having substantially the same calculated position information of the detected boundaries of the atrium.

As another example, boundaries of a blood vessel may be detected from the plural X-ray images, position information of the detected boundaries of the blood vessel may be calculated, and the plural X-ray images may be grouped into X-ray images having the same calculated position information of the detected boundaries of the blood vessel.

As another example, a blood vessel may be detected from the plural X-ray images, the widths of the detected blood vessel may be calculated, and the plural X-ray images may be grouped into X-ray images having the same calculated width of the blood vessel.

As a further example, a blood vessel area may be detected from the plural X-ray images, a brightness distribution histogram of the detected blood vessel area may be calculated, and the plural X-ray images may be grouped into X-ray images having the same brightness distribution of the blood vessel area based on a result of calculation.

When X-ray image grouping has been completed, at least one group of a plurality of groups is selected at Operation S530. Group selection may be performed by instructions or a command input by an operator. If the operator inputs no instructions or command, a designated portion of the groups (e.g., all groups or a subset of the groups) may be selected.

Thereafter, 3D volume data of each of the selected groups is acquired by performing image reconstruction of each of the selected groups at Operation S540. The 3D volume data acquired by performing image reconstruction of each of the selected groups clearly displays an area around the heart.

When the 3D volume data of each of the selected groups has been acquired, volume rendering of each set of the 3D volume data is performed at Operation S550. According to an exemplary embodiment, volume rendering of each set of the 3D volume data may be performed at the same point of view.

As one example, Operation S550 may include acquiring a plurality of 2D projection images by performing volume rendering of each set of the 3D volume data at the same point of view.

As another example, Operation S550 may include acquiring a left image and a right image of each set of the 3D volume data by performing volume rendering of each set of the 3D volume data at two points of view corresponding to left and right eyes of a human, and acquiring a plurality of 3D stereo images based on the acquired left and right images of each set of the 3D volume data.

When volume rendering has been completed, a result of the volume rendering may be displayed at Operation S560. Operation S560 may include at least one of displaying the plurality of 2D projection images and displaying the plurality of 3D stereo images.

As is apparent from the above description, in an X-ray imaging apparatus and a control method thereof in accordance with exemplary embodiments, plural chest X-ray images are grouped according to cardiac phases and image reconstruction of each group of the acquired groups (or a selected portion of the groups) is performed, thus improving the quality of 3D volume data acquired as a result of image reconstruction.

Since the 3D volume data of each of the groups is acquired, a cardiac output may be calculated based on the acquired 3D volume data of each of the groups.

A plurality of 2D projection images or a plurality of 3D stereo images is acquired by performing volume rendering of each set of the acquired 3D volume data, and the plural 2D projection images are sequentially displayed or the plural 3D stereo images are sequentially displayed, thus allowing an operator to detect heart abnormalities.

Although a few exemplary embodiments have been shown and described, it would be appreciated by those skilled in the art that changes may be made in these exemplary embodiments without departing from the principles and spirit of the invention, the scope of which is defined in the claims and their equivalents.

What is claimed is:

1. An X-ray imaging apparatus comprising:
    an image processor configured to acquire a plurality of X-ray images of an object from converted electrical signals, group the plurality of X-ray images into groups of X-ray images acquired from the same cardiac phase, and perform image reconstruction of each of the groups acquired as a result of the grouping to thereby generate 3D volume data of the object,
    wherein the image processor is configured to group the plurality of X-ray images into the groups based on information regarding a blood vessel connected to the object, the groups comprising a first group of X-ray images obtained when the blood vessel has a first width and a second group of X-ray images obtained when the blood vessel has a second width different from the first width.

2. The X-ray imaging apparatus according to claim 1, further comprising an X-ray generator configured to radiate the X-rays to the object from different positions, wherein the X-ray generator is movable to the different positions.

3. The X-ray imaging apparatus according to claim 1, further comprising an X-ray generator configured to radiate the X-rays to the object from different positions, wherein the X-ray generator is fixed at each of the different positions.

4. The X-ray imaging apparatus according to claim 1, wherein the image processor is further configured to detect a cardiac area from the plurality of X-ray images and group the plurality of X-ray images based on at least one of shapes of the detected cardiac area and brightness distributions of the detected cardiac area.

5. The X-ray imaging apparatus according to claim 1, wherein the image processor is further configured to detect boundaries of an atrium from the plurality of X-ray images and group the plurality of X-ray images based on position information of the detected boundaries of the atrium.

6. The X-ray imaging apparatus according to claim 1, wherein the image processor is further configured to detect boundaries of the blood vessel connected to the object from the plurality of X-ray images and group the plurality of X-ray images based on at least one of position information of the detected boundaries of the blood vessel and brightness distributions of the detected blood vessel.

7. The X-ray imaging apparatus according to claim 1, wherein the image processor is further configured to select at least one of the groups acquired as a result of the grouping and perform image reconstruction of each group of the at least one selected group.

8. The X-ray imaging apparatus according to claim 1, wherein the image processor is further configured to generate a plurality of 2D projection images by performing volume rendering of the 3D volume data at a designated point of view.

9. The X-ray imaging apparatus according to claim 8, further comprising a display configured to display the plurality of 2D projection images.

10. The X-ray imaging apparatus according to claim 1, wherein the image processor is further configured to acquire left and right images of the 3D volume data by performing volume rendering of the 3D volume data at a left point of view and a right point of view, and acquire a plurality of 3D stereo images by combining the left and right images of the 3D volume data.

11. The X-ray imaging apparatus according to claim 10, further comprising a display configured to display the plurality of 3D stereo images.

12. A control method of an X-ray imaging apparatus, the control method comprising:
    radiating X-rays to an object from different positions using an X-ray generator;
    detecting X-rays transmitted through the object and converting the detected X-rays into electrical signals using an X-ray detector;
    acquiring a plurality of X-ray images of the object based on the converted electrical signals;
    grouping the plurality of X-ray images into groups of X-ray images acquired from the same cardiac phase; and
    performing image reconstruction of each of the groups acquired as a result of the grouping to thereby generate 3D volume data of the object,
    wherein the grouping comprises grouping the plurality of X-ray images into the groups based on information regarding a blood vessel connected to the object, the groups comprising a first group of X-ray images obtained when the blood vessel has a first width and a second group of X-ray images obtained when the blood vessel has a second width different from the first width.

13. The control method according to claim 12, wherein the grouping of the plurality of X-ray images further includes:
    detecting a cardiac area from the plurality of X-ray images; and grouping the plurality of X-ray images based on at least one of shapes of the detected cardiac area and brightness distributions of the detected cardiac area.

14. The control method according to claim 12, wherein the grouping of the plurality of X-ray images further includes:
   detecting boundaries of an atrium from the plurality of X-ray images; and
   grouping the plurality of X-ray images based on position information of the detected boundaries of the atrium.

15. The control method according to claim 12, wherein the grouping of the plurality of X-ray images further includes:
   detecting boundaries of the blood vessel connected to the object from the plurality of X-ray images;
   calculating at least one of position information of the detected boundaries of the blood vessel and brightness distributions of the detected blood vessel; and
   grouping the plurality of X-ray images based on a result of the calculating.

16. The control method according to claim 12, wherein the grouping of the plurality of X-ray images further includes:
   selecting at least one of the groups acquired as a result of grouping; and
   performing image reconstruction of each group of the at least one selected group.

17. The control method according to claim 12, further comprising:
   generating a plurality of 2D projection images by performing volume rendering of the 3D volume data at a designated point of view; and
   displaying the plurality of 2D projection images.

18. An imaging device, comprising:
   an X-ray generator configured to transmit X-rays towards a living object;
   an X-ray detector configured to detect a portion of the X-rays transmitted through the living object; and
   an image processor configured to generate X-ray images based on the detected X-rays and group the X-ray images into groups according to a cardiac cycle of a heart of the living object, to thereby generate 3D volume data of the living object,
   wherein the image processor is configured to group the X-ray images into the groups based on information regarding a blood vessel connected to the heart of the living object, the groups comprising a first group of X-ray images obtained when the blood vessel has a first width and a second group of X-ray images obtained when the blood vessel has a second width different from the first width.

19. The imaging device according to claim 18, wherein the image processor is configured to group the X-ray images such that each of the groups corresponds to a different respective cardiac phase of the living object.

20. The imaging device according to claim 19, wherein the image processor is further configured to:
   select at least one of the groups as a target for image reconstruction, and perform the image reconstruction on the selected at least one group to thereby obtain the 3D volume data.

* * * * *